United States Patent [19]

Khanna et al.

[11] Patent Number: 5,188,938
[45] Date of Patent: * Feb. 23, 1993

[54] ENZYME QUANTITATION WICKING ASSAY

[75] Inventors: Pyare L. Khanna, Fremont; Glenda L. Choate, Concord, both of Calif.

[73] Assignee: Microgenics Corporation, Concord, Calif.

[*] Notice: The portion of the term of this patent subsequent to Aug. 6, 2008 has been disclaimed.

[21] Appl. No.: 777,489

[22] Filed: Oct. 15, 1991

Related U.S. Application Data

[63] Continuation of Ser. No. 291,457, Dec. 29, 1988, abandoned.

[51] Int. Cl.$^5$ ............... G01N 33/535; G01N 33/558; G01N 33/537
[52] U.S. Cl. .................................. 435/7.7; 435/7.6; 435/7.92; 435/18; 435/970; 435/975; 422/56; 422/57; 436/518; 436/514; 436/531; 436/538
[58] Field of Search ............ 435/7.6, 7.9, 7.92, 435/18, 970, 975, 174, 177, 180; 436/500, 514, 531, 518, 536, 538; 422/55, 57

[56] References Cited

U.S. PATENT DOCUMENTS

| | | | |
|---|---|---|---|
| 4,708,929 | 11/1987 | Henderson | 435/7 |
| 4,740,468 | 4/1988 | Weng et al. | 436/501 |
| 4,818,677 | 4/1989 | Hay-Kaufman et al. | 435/4 |
| 4,937,188 | 6/1990 | Giese et al. | 435/41 |
| 5,037,735 | 8/1991 | Khanna et al. | 435/7.6 |

OTHER PUBLICATIONS

Langley, et al., "β-Galactosidase α Complementation Properties of the Complemented Enzyme and Mechanism of the Complementation Reaction" in *Biochemistry* (1976) 15(22):4866–4875.

*Primary Examiner*—Esther L. Kepplinger
*Assistant Examiner*—Carol E. Bidwell
*Attorney, Agent, or Firm*—Cooley Godward Castro Huddleson & Tatum

[57] ABSTRACT

Diagnostic assays are provided comprising complementary enzyme fragments of β-galactosidase, where one of the fragments is bound to a support and the other fragment is conjugated to an immunologically cross-reactive epitope of the analyte or complementary to an analyte receptor. Binding to the receptor allows for discrimination between complexed enzyme fragment conjugate and uncomplexed enzyme fragment conjugate. The assay medium is then allowed to wick onto a support to which the complementary fragment is substantially uniformly bound in the detection region. The support is then developed, where color formation from the substrate in the detection region is used as a measure of the presence of analyte in the sample.

10 Claims, No Drawings

ENZYME QUANTITATION WICKING ASSAY

CROSS-REFERENCE TO RELATED APPLICATIONS

This application is a continuation of U.S. application Ser. No. 07/291,457, filed Dec. 29, 1988, now abandoned.

TECHNICAL FIELD

The present invention relates to specific binding pair assays and, employing $\beta$-galactosidase fragment complementation and complex separation.

BACKGROUND OF THE INVENTION

A wide variety of immunoassays have been based on competitive inhibition where analyte in the sample competes with a known amount of labeled analyte for a fixed amount of anti-analyte antibody. Enzyme labels are often used in competitive inhibition assays, where binding of anti-analyte antibody with an enzyme-analyte conjugate allows for separation of complexed and uncomplexed conjugate.

An assay has been reported, based on the ability of fragments of $\beta$-galactosidase to complement and form active enzyme. In particular, a $\beta$-galactosidase enzyme donor (ED) combines with a $\beta$-galactosidase enzyme acceptor (EA) to form an active $\beta$-galactosidase enzyme. Conjugating a small analyte or an analyte analogue to the ED at certain sites does not affect the rate of $\beta$-galactosidase catalyzed activity. However, when the ED-analyte conjugate is bound by anti-analyte antibody, the enzyme-catalyzed reaction rate during the initial phase of the reaction is reduced. This reduction in enzyme-catalyzed reaction rate has been used to quantitate the determination of a plurality of analytes where ED-analyte conjugate present in an assay medium and analyte present in the sample compete for anti-analyte antibody prior to the addition of EA. The $\beta$-galactosidase-catalyzed reaction rate increases as the amount of analyte present in the sample increases.

Although the assays can be performed in a hospital or other clinical laboratory setting, there is a need for simplified assay protocols which can be performed by relatively unskilled personnel and analyzed without the use of sophisticated equipment.

RELEVANT LITERATURE

Modified $\beta$-galactosidase enzyme donors and enzyme acceptors have been prepared by chemical synthesis and recombinant engineering. The modified fragments retain $\beta$-galactosidase activity upon complementation and facilitate production of and attachment of analyte to the fragments. See for example U.S. Pat. No. 4,708,929 and the articles cited therein.

SUMMARY OF THE INVENTION

A wicking assay is provided employing complementary fragments of $\beta$-galactosidase as the label. One of the $\beta$-galactosidase complementary fragments is bound to a bibulous surface, while the other is conjugated to an epitope immunologically cross-reactive with a ligand analyte or complementary to a receptor analyte. Transfer to the bibulous member allows for transport of the receptor complexed complementary member away from uncomplexed complementary member. When the uncomplexed complementary member binds to the other enzyme fragment, color can be developed with substrate at the site of such binding. The determination of the presence of uncomplexed enzyme fragment conjugate may be as a result of prior separation of complexed from uncomplexed enzyme conjugate or discrimination between complexed and uncomplexed enzyme conjugate on the bibulous member.

DESCRIPTION OF THE SPECIFIC EMBODIMENTS

A wicking assay is provided where complementary $\beta$-galactosidase fragments are employed, where one fragment is conjugated to an epitope which is either cross-reactive with an epitope of an analyte or specifically binds to a receptor analyte. The other fragment is non-diffusibly bound to a bibulous member which allows for transport of an aqueous medium. The two fragments are referred to as the enzyme donor, which is generally the smaller fragment and comprises at least a portion of the N-proximal portion of the $\beta$-galactosidase enzyme, and the enzyme acceptor which is usually the larger fragment and is the C-proximal portion of the $\beta$-galactosidase enzyme. The enzyme donor and enzyme acceptor are abbreviated as "ED" and "EA," respectively. For a complete description of the enzyme system, see U.S. Pat. No. 4,708,929.

The components of the assay are the enzyme fragment conjugate, the support-bound enzyme fragment, the enzyme substrate, and the assay medium. A number of different protocols may be employed, whose selection may be affected by the nature of the analyte.

In carrying out the assay, the sample, conjugate and receptor, which may be the analyte, are combined in an appropriate assay medium. Where the analyte is a ligand, the receptor may be bound to a solid support, so as to allow for physical separation of conjugate which binds to receptor to form a complex, or may be free in solution, where the complex will be applied to the bibulous member. In some instances, where the complex is free in solution, it may be preformed prior to combining with the sample.

After sufficient time for reaction to occur between the sample and receptor, the assay medium may then be contacted with the bibulous member. The contact may be at a site proximal to one end of an elongated strip, where the assay medium will then migrate at least a substantial proportion of the length of the strip or may be applied at a site, where the assay medium may radiate outwardly from the site of application, so as to substantially uniformly radiate from the site of application. At such time as no further addition of assay medium is made to the bibulous member, migration will terminate and the bibulous member may be contacted with a substrate solution. Usually, the region comprising from the site of application to the solvent front will be contacted with the substrate. Contact with the substrate solution may then be terminated and the reaction will continue until the solvent has substantially evaporated, so that no further reaction may occur.

As indicated, the format of the assay may differ, depending upon the nature of the analyte. With hydrophilic analytes, it will usually be preferable to have a prior separation of complexed enzyme fragment conjugate from uncomplexed enzyme fragment conjugate, so that the bibulous member will not encounter complexed enzyme conjugate. Separation may be achieved by providing for receptor bound to a solid support, which may be the walls of a vessel, such as a microtiter plate, particles, e.g. Sephadex particles, cells or the like, or provide for oligomerization of the complex, by having polyvalent anti-receptor, which can form very high molecular weight aggregates of the complex which will not migrate from the site of contact with a bibulous member and would have substantially reduced, if no activity, in forming an active enzyme.

Alternatively, where an elongated strip is employed, one could have the site which initially contacts the assay medium conjugated with antireceptor, so as to capture the receptor. The presence of the complementary enzyme fragment displaced by the sample would be displaced from the region of the antireceptor.

Where the analyte is hydrophobic, or the conjugate is made hydrophobic by bonding of a hydrophobic group to the enzyme fragment, that is a hydrophobic molecule other than the analyte, separation of the complexed conjugate and uncomplexed conjugate prior to contact with the bound enzyme fragment is not required. When the assay medium is contacted with the bibulous support, the hydrophobic uncomplexed conjugate is retained in a relatively small region near the site of contact, while the complexed member migrates away from the site of contact. Color development, when the bibulous member is contacted with the substrate, is much more intense at the site where the complementary enzyme fragments bind to form active enzyme. The presence of the receptor bound conjugate results in migration with the solvent and binding to EA away from the site of application providing for a larger detectable region. This format has particular application with threshold assays, where the primary interest is the presence of an analyte above or below a threshold concentration.

The ED and EA fragments and their conjugates are amply described in U.S. Pat. No. 4,708,929, which disclosure is incorporated herein by reference. Therefore, there is a need only for a brief description of the ED and EA. The ED will usually be from about 60 to 100 amino acids and will generally be modified by fusion with an amino acid sequence providing an epitope of interest or a mutation providing for a cysteine or lysine, which provide for a mercapto or amino functional group for conjugation. The method of preparation of the EA may be isolation from a naturally occurring mutant source, or the EA may be synthesized by recombinant techniques, where available functionalities may be employed for conjugation or a cysteine introduced into the sequence to provide for a useful site for conjugation. Any of the numerous EDs and EAs described in U.S. Pat. No. 4,708,929 may be employed.

The choice of the bibulous support will depend upon a number of considerations. The bibulous support should allow for non-diffusible binding of the enzyme fragments to the support, either covalently or non-covalently. The support should not interfere with the required migration of the assay components or the support may be modified to provide for the necessary properties. That is, the support should not result in significant non-specific binding or the support may be treated to avoid such non-specific binding.

Numerous bibulous solid supports used in immunoassay wicking methods are reported in the literature, which include modified cellulosic supports such as paper, nitrocellulose and desirably, non-cellulosic supports such as nylon membranes, polyester-based membranes and polyamide-based membranes. Conveniently, the solid support will be a chemically-reactive membrane, such as a treated nylon membrane, that covalently or non-covalently binds proteins incubated with the membrane. Nylon membranes which covalently bind proteins, apparently through formation of a bond with protein amino groups, are commercially available from sources including Millipore Corporation ("Immobilon") and Pall Corporation ("Immunodyne"). Immunodyne membranes are preferred as membrane-affixed EA are found to be stable for longer periods upon storage with Immunodyne membranes than with Immobilon membranes.

The enzyme fragment will be bound to the solid support by conventional means for covalently or non-covalently attaching a protein to the support material. A preferred method for attaching EA to Immobilon membranes is described in detail in the Experimental section. Conveniently, the enzyme fragment may cover the entire surface of the solid support, but will at least cover the region where color formation is determined. Desirably, the enzyme fragment will be on the surface of the paper at a substantially uniform concentration. This can be achieved by dipping, spraying, knife-blade application, or the like. After attachment of the enzyme fragment, the support will usually be coated with a blocking agent, usually a protein, such as bovine serum albumin (BSA) or casein, to minimize non-specific binding of proteinaceous substances to the support. Generally, the protein containing solution will be at a concentration in the range of about 0.05 to 5 wt percent, more usually, 0.1 to 1 wt percent. The support will be carefully washed, desirably with an aqueous buffer solution containing a surfactant, to remove enzyme fragment which is not tightly bound to the support.

Following preparation, the support is blotted dry and stored, desirably in a vacuum desiccator. Storing the support under dry conditions has been found to enhance the stability of EA. The support may be stored for extended periods at room temperature or refrigerated for longer stability. Stabilizers may be applied, such as sugars.

The support may be prepared as large sheets, which may then be further processed to provide for strips, circular pads, rectangular pads, or the like. The strips may include a rigid member for support and ease of manipulation. Numerous strips and pads are described in the literature concerned with diagnostic assays, which articles may be employed in the subject invention. The pads will usually be substantially symmetrical, as compared to the strips, having the smallest surface dimension greater than about 3 mm and less than about 2 cm.

In the case of strips, these strips may be subjected to further treatment to provide for a separation region. As already indicated, the region proximal to the site of contact with the assay medium may provide for separation of conjugate complexed with receptor. Thus, by having anti-receptor in the region, any complexed enzyme fragment conjugate will be retained in that region and prevented from transport to the next region, where the complementary enzyme conjugate is bound.

The amount of enzyme fragment on the support may be varied, normally being in substantial excess in total amount to the amount of complementary enzyme fragment conjugate in the assay medium. The particular concentration on the surface of the support will vary depending upon the particular assay, binding affinity of the enzyme fragment conjugate, as well as the format of the assay. The concentration of the solution employed to impregnate the support with the enzyme fragment will generally be in the range of about 1 to 100µM, more usually in the range of about 5 to 75µM. Conveniently, the enzyme conjugate will be applied to the support in an aqueous buffered medium, generally buffered to a pH in the range of about 6.5 to 8, with buffer concentration in the range of about 50 to 250µM. Any conventional buffer may be employed, such as Tris, phosphate, acetate, MOPS, HEPES, or the like.

The assay medium will comprise the enzyme fragment conjugate, the sample, and when the analyte is other than receptor, receptor for the analyte. As already indicated, a receptor may be bound to a support or may be dispersed in solution. The amount of enzyme fragment conjugate will vary with the concentration range of interest of the analyte. Normally, the enzyme fragment conjugate will be in the range of about the highest concentration of analyte in the range of interest. The particular concentration will be selected to provide for a desired signal level in the concentration range of interest, and where the range is quantitated, sufficient sensitivity to be able to distinguish between significant differences in concentration, while minimizing background level and other interferences.

This concentration is desirably determined in solution by studying the kinetics of the reaction. See, for example, copending application Ser. No. 151,412 filed Feb. 2, 1988, now abandoned, which describes in detail optimizing conjugate and antibody concentrations so that the assay responds to an analyte dose in the anticipated concentration range. Usually, the concentrations of complementary specific binding pair member and conjugate will be within at least 85%, more usually within at least 95% of the concentration necessary to optimize conditions.

After the optimal complementary specific binding pair member and conjugate concentrations in the desired analyte concentration range are determined in a solution assay, those concentrations may be used in the subject wicking assay.

The buffer formulation is not critical. In general, physiological buffers such as phosphate buffered saline, Tris buffer and like buffers are useful. A preferred buffer comprises about 100 mM to about 300 mM NaPO$_4$, about 5 mM to about 10 mM EGTA, and about 10 mM to 20 mM NaN$_3$ having a pH of between 6 and 8. The temperature for the assay will usually be at least about 20° C., preferably elevated, but below 60° C. Most assays are performed at about 20° C. to about 30° C. or at an elevated temperature of about 37° C. The assays are performed at atmospheric pressure.

The sample may be obtained from any source of interest, including physiological fluids, such as blood, serum, plasma, spinal fluid, vitreous humor, etc., chemical processing effluents or reaction mixtures, water sources, air sources, or the like. The particular source of sample is not critical to this invention. The sample may be subject to prior treatment or no prior treatment. The sample may be subject to dilution or may be used as is. For the most part, the sample will usually be less than about 50%, by volume of the assay medium. Usually, the sample will range from about 0.1 to 20 vol% of the assay medium. In case of dilution, the sample will normally be combined with a buffered medium, which is buffered to provide a pH in the range of about 6 to 8 after mixing with the sample. Usually, the enzyme fragment conjugate will be combined with the sample as a solution, rather than as a dry powder. The receptor, may be present as a preformed complex with enzyme conjugate, where the receptor which is present will be generally present in sufficient amount to bind substantially all of the enzyme conjugate. The ratio of receptor to enzyme conjugate will allow for competition with analyte in the sample, so that the amount of uncomplexed enzyme fragment conjugate which is present will be related to the amount of analyte in the assay medium. The amount of receptor employed in the assay medium will be at least substantially optimized in accordance with the sensitivity of the assay.

After combining the various components of the assay medium, the assay medium will normally be incubated for at least about 0.5 min, and not more than about 120 min, usually for about 3 to 60 min. The temperature of the incubation will usually be within the temperature range employed for the reaction on the support.

After the incubation period, the support will be brought into contact with the assay medium. Where any elongated strip or dipstick is employed, the assay medium may be contacted with the strip proximal to or at one end or ed9e of the strip. The end of the strip may be immersed in the medium or maintained at the surface of the medium, to allow for wicking. This may be performed by placing the strip in a tube or microtiter plate well, which served as the assay reaction vessel.

Alternatively, an aliquot of the assay medium may be placed on a glass slide or other surface and the dipstick suspended above the drop of assay medium. The assay medium will be drawn or wicked vertically up the dipstick by the contact with the dry support. Conveniently, not more than about 100 µl usually about 20 to about 25 µl, will be used. The assay medium volume will conveniently be a somewhat larger volume than that required to travel a predetermined length up the support, which length will desirably be at least about 50% and less than 100% of the length of the strip, desirably about 75% to about 90%. The small amount of assay medium necessary permits the use of very small sample volumes and avoids wasting assay reagents. However, substantially larger assay medium volumes may be used when desired for convenience of measurement or the like.

After the assay medium solvent front has traveled to a predetermined height on the strips, the strips will be incubated for about 5 to about 30 min., more usually about 10 to 30 min., depending upon the temperature. Usually incubation will be for a time sufficient for EA to react with ED to form solid support-affixed β-galactosidase.

Where the assay medium is placed at a central site and radiates outwardly from the site, the assay medium may be applied to the site by capillary, dropper, or other convenient means. The liquid will then radiate outwardly from the site to a distance depending upon the volume applied at the central site. The addition may be continuous or interrupted.

The support is thereafter incubated with an enzyme substrate solution. An enzyme substrate is employed that when cleaved by the enzyme results in a visually detectable change in the amount of light absorbance (optical density) or emission on the support. That is, cleavage of the substrate results in the appearance or disappearance of a colored or fluorescent product, normally with retention of the product at its generation site. The enzyme substrate may produce a precipitating product. A preferred enzyme substrate is chlorphenol red galactoside (CPRG). CPRG and other comparable enzyme substrates such as orthonitrophenyl-β-D-galactoside (ONPG) are commercially available. Incubation with enzyme substrate is conveniently performed by immersing the support in the enzyme substrate solution. When using CPRG, the support will conveniently be incubated for from 1 to 10 min. at room temperature in a solution of between about 0.5 to 2mM CPRG. EA may be added to the substrate solution to enhance color development, if desired.

Where a strip is used, the distance to which color formation occurs, normally in proportion to the distance of a solvent front, or the change in intensity of color, will be related to the amount of analyte in the sample medium. Where, however, the support provides for application at a single site and radiation outward, with a hydrophobic analyte, one will normally observe a deeper color at a site proximal to the site of application of the assay medium as compared to regions removed or distal from such site. In the distal region, the color production is related to the amount of analyte in the medium. In this situation, one will usually be concerned with a threshold value, so that the development of color in the proximal region will indicate the presence of the analyte above a predetermined concentration. Where the enzyme fragment conjugate is hydrophilic, then the complexed enzyme conjugate will have been previously removed from the assay medium or be inactivated, so that the diameter or color intensity of the colored region will be proportional to the concentration of analyte in the medium.

Various protocols may be employed, some of which may have been already indicated. For example, buffered sample may be added to ED-conjugate bound to antibody covalently bonded to the walls of a microtiter plate well. After sufficient time for incubation, an aliquot of the assay medium is transferred to a support to which EA is conjugated at a designated site and the medium allowed to migrate until no further migration occurs and the support allowed to dry. The substantially dry support is then dipped into a solution of enzyme substrate which produces a colored product and removed from the enzyme substrate solution and allowed to dry. The height or color intensity is determined as a measure of the amount of analyte in the medium.

In the next embodiment, the analyte is a hydrophobic analyte, such as thyroxine. A soluble complex of the ED-thyroxine conjugate and antithyroxine or thyroxine binding globulin is combined with the sample and incubated for sufficient time for any thyroxine to displace the conjugate from the complex. An aliquot of the assay medium is then spotted at a site on a support conjugated with EA and solvent allowed to migrate and the support dried. The support is then dipped into enzyme substrate solution, removed and allowed to dry. The presence of a dark spot at the site of the application of the assay medium as compared to the region surrounding that site is indicative of a concentration of thyroxine above a threshold concentration in the assay medium. The conjugate-antibody complex is capable of migrating away from the site of application and provides for active enzyme while the hydrophobic conjugate remains substantially at the site of application In a further embodiment, hydrophilic EA-analyte conjugate as an antibody complex is combined with the sample and incubated for sufficient time for the mixture to reach equilibrium. A strip is used which has a region at one end to which anti-antibody is present in sufficient amount to bind all of the antibody in the assay medium. The remainder of the strip is conjugated to ED. The end of the strip to which the anti-antibody is bound is immersed in the assay medium and the assay medium allowed to migrate, so that the solvent front reaches a predetermined distance. The strip is then removed from the assay medium, allowed to dry and immersed in enzyme substrate solution. The strip is removed from the enzyme substrate solution and allowed to develop and the distance of the color front determined. The distance or color intensity is proportional to the amount of analyte in the assay medium.

To facilitate performing the subject assays, kits may be provided. Components of the kit will include the bibulous support to which an enzyme fragment has been non-diffusibly bound, an enzyme-fragment conjugate, comprising a cross-reacting epitope with the analyte or a complementary epitope where the analyte is a receptor, and optionally the receptor to a ligand analyte. The conjugate and receptor may be provided separately or as a single reagent. In some instances, it may be desirable to provide for receptacles, where the receptor is bound to the walls of the receptacle. In addition, one or more analyte controls may be provided having a known concentration of anaylte in the anticipated sample concentration range. Other than the support, the other reagents may be provided in liquid or dry form.

The following examples are offered by way of illustration and not by way of limitation.

EXPERIMENTAL

Example 1

Preparation of EA Paper

To bind EA to membranes, the membranes were shaken for 30 min. at room temperature (RT) covered in a solution of EA22 5–10 $\mu$M in 50mM $PO_4^{3-}$ buffer pH 7.4. The membranes were then blocked with a solution of 1% casein in PBS (shaking, 60 min., RT), followed by two rinses in PBS containing 0.05% Tween 20 (shaking, 15 min., RT). The membranes were then blotted dry and stored in a vacuum desiccator.

For complete binding of proteins to occur, it is preferable that there are no thiols to compete for protein binding sites on the membrane. Thus, the EA used for the following examples was "exchanged" EA22 in which the storage thiols were removed by passage over a Sephadex column.

Exchanged EA was stored for up to 7 days refrigerated with or without the addition of EGTA for thiol protection or was frozen with 10% glycerol for storage of 7 or more days to provide for comparable enzyme activity following immobilization.

Example 2

Behavior of ED4 using Radial vs Vertical Wicking Methods with Pall-EA Membranes ED4 (0.06 to 1.0 $\mu$M) was spotted and allowed to radially wick on Pall membranes prepared with 5$\mu$M or 20 $\mu$M EA. As the concentration of ED or immobilized EA increased, the color density of the chlorophenol red (CPR) spot increased, as was seen with the experiments using ED4T4 (see Example 8). However, in all the samples, the spot of CPR formation was the same diameter as the solvent front. This indicates, unlike ED4T4, that the Pall-EA membranes did not preferentially hold back ED4.

The same experiment was performed in the vertical wicking mode. There were only slight increases in the height of the CPR reactive front as the concentration of ED increased unless the ED4 concentration was increased over 1.0 μM. Unlike the radial mode, the reactive front did not reach the same height as the solvent front until very high concentrations of ED4 were used. Again, the density of color increased when either the ED4 concentration or immobilized-(EA) concentration was increased.

Example 3

Behavior of ED4 with Pall-EA Blocked by Various Agents

Since CPRG binds non-specifically to Pall-EA membranes, a study was performed to determine whether or not ED4 was binding specifically to the EA of the blocked Pall-EA membranes, or whether there was non-specific binding due to poor blocking of the membranes. Pall-EA membranes prepared with 10 μM EA were blocked with 1% BSA or with 0.1% or 1% casein. A solution of 5 μM ED4 was allowed to wick vertically with these membranes and the reaction was monitored as usual. When BSA-blocked membranes were used, the CPR reactive front was only one-half the height of the solvent front; whereas, the reactive front was identical with the solvent front with either of the casein-blocked membranes. These results indicated that the BSA-blocked membranes did not allow excess ED4 to wick as effectively as did the casein-blocked membranes.

The behavior of ED4 was also studied on Pall membranes which were simply blocked and rinsed, without EA being immobilized. A solution of 10 nM ED4 was allowed to wick vertically with the blocked membranes. The membranes were then incubated with CPRG containing EA to detect the height of the ED4 wicking. The casein-blocked membranes allowed the ED4 to wick along with the solvent front; whereas, ED4 wicked to less than one-half the height of the solvent front when the BSA-blocked membranes were used. At this point, the use of casein as a blocking agent was further studied.

Example 4

Optimization of Casein Concentration

The following studies were performed to determine the optimal concentration of casein for blocking. A solution of 10 μM ED4 was found to wick higher with 1% casein vs 0.1% casein blocked Pall-EA membranes. When ED4 was allowed to wick on non-EA Pall membranes and then rinsed before assay, no CPR formation was found with either concentration of casein-blocking. This indicated that either concentration of casein prevented tight non-specific binding of ED4 to non-EA membranes.

The next attempt to determine the optimal casein concentration for blocking involved preparing Pall membranes with either 1 or 10 μM EA immobilized and with either 0.1% or 1% casein in the blocking step. If ED4 is being withheld specifically by EA immobilized onto the membranes, the height reached by ED4 would be higher as the EA concentration decreased. That is, less EA immobilized would allow ED4 to wick closer to the solvent front. With 1% casein-blocked EA membranes, there was no difference in ED4 height reached when comparing 1 vs 10 μM EA-membranes; whereas, the height of ED4 wicking was slightly higher for the 1 μM EA vs 10 μM EA membranes which were blocked with only 0.1% casein. An optimal membrane allows ED4 to wick higher as the concentration of ED4 is increased; however, all the membranes prepared still yielded poor correlation of ED4 height vs ED4 concentration. In addition, the height to which ED4 rose was not a well-defined line. This was determined by varying the assay conditions for the ED4 height. After varying concentrations of ED4 were allowed to wick vertically on the various EA-membranes, the membranes were either dipped into CPRG, as usual, or into CPRG containing additional EA. The CPR reactive front was higher in the latter case, indicating that ED4 had actually reached a height greater than seen when no EA was present with the CPRG. That is, ED4 apparently traveled as a gradient, with a small amount ahead of the main band. The presence of additional EA in the CPRG provided the sensitivity to detect this small amount of ED4 wicking ahead of the main ED4 front.

Example 5

Properties of ED4 with 1% Casein-Blocked Pall-EA

The 1% casein-blocked Pall-EA (10 μM EA) was chosen to determine if a migratory assay could be achieved with ED4; that is, can increasing ED4 concentration in the sample be correlated with an increase in the height to which ED4 wicks. The protocol involved wicking 3 to 30 nM ED4 with the Pall-EA membranes, incubating at 37° C. for 10 min., dipping into CPRG, then allowing to develop at room temperature (RT) with or without sealing the membranes in a moisture-tight container. The membranes which were sealed dried more slowly than the membranes in the unsealed containers, allowing the reaction to go further to completion and yielding darker color height discrimination vs ED4 concentration.

Since 3 nM ED4 rose to over one-half the solvent front height, the experiment was repeated at a lower range of ED4 concentration (0.6 to 2.4 nM). The height discrimination between the various concentrations of ED4 was poor, but there was good correlation with color intensity.

Example 6

Binding Capacity of Pall-EA Membranes

A study was designed to determine whether increasing the concentration of EA bound to the membranes would bind ED4 more effectively and provide better correlation of vertical wicking distances and ED concentration. A series of Pall-EA membranes was prepared using 6, 23, or 42 μM EA solutions for binding to the membranes. These membranes were assayed with varying concentrations of ED4 in both the vertical and radial wicking modes. When the ED4 concentration was held constant, the height attained with the 23 μM EA membrane was lower or similar to that with the 6 μM EA membrane. Both attained greater heights than using the 42 μM EA samples. However the sensitivity of the higher concentration EA-Pall membrane allowed the extra ED4 height to be detected. The height attained with the 42 μM EA sample was actually the lowest, since the additional EA immobilized to the membrane bound the ED4 more effectively.

Example 7

Stability of ED Binding to EA

The next experiment was designed to test the strength of the bond between the ED4 and immobilized EA. ED4 (2nM) was allowed to vertically wick with a wide strip of Pall-EA. The strip was immediately cut in half lengthwise. One-half was incubated at 37° C, 10 min, as usual, and then dipped into CPRG. The other half was used to challenge the ED4 binding with a rinse. The first solvent front was not allowed to wick to the top of the membrane, so that the membrane (after the initial ED4 wicking) could be put into a solution of Tween-PBS, (50 mM $NaPO_4$ pH 7.0 to 7.5, 0.05% Tween) which caused the initial solvent front to move some additional distance. When this strip was incubated and developed, the identical height of ED4 was reached as the first strip. Thus, the original ED4 binding to immobilized EA was not removed by the subsequent rinsing step.

Example 8

Hydrophilicity of Conjugates

Various concentrations of ED4T3 (1 to 100nM) were spotted and allowed to wick radially with Pall membranes which had not been incubated with EA but which had been blocked with 1% casein. The membranes were developed with EA and CPRG. In all cases, the color was restricted to a central dot, which did not reach the solvent front. Thus, the blocked-Pall membranes did not allow wicking of ED4T3 to the solvent front, although in previous studies ED4 wicked to the solvent front. This non-specific binding of conjugate was attributed to the hydrophobic nature of the ED-T3 conjugate and a series of other conjugates was studied to determine the degree of hydrophilicity required for the conjugate to wick with the assay medium unless bound by EA.

EA paper, prepared by reacting Pall membranes with 5 μM EA, was spotted with 3 to 5 μl of 10 nM solutions of various conjugates. As in the earlier study, the ED4 spot extended to the solvent front, while ED4T3 remained as a small dot. ED4T4 behaved identically to ED4T3. ED4-Digoxin remained in the center, although the radius was larger than the T3 and T4 conjugate spots. ED4-B12 extended to the solvent front. Solutions of ED4-KLH and ED4-BSA, though poorly reactive, also extended to the solvent front.

These results demonstrate that the amount of conjugate migration in the absence of antibody correlates directly with the hydrophilicity of the conjugate. That is, the T3 and T4 conjugates are the most hydrophobic, followed by the digoxin conjugate and these are the only conjugates which did not wick with the solvent front.

Example 9

ED4-B12 Assay

The studies with ED4T3 described in Example 8 were repeated with conjugates which are more hydrophilic than ED4T3. ED4-B12 was incubated with a range of concentrations of anti-B12 antibody (1:5000 to 1:100 dilutions) to form immune complexes. Those complexes were assayed in solution to determine inhibition of complementation and were spotted on Pall-EA paper. At the lowest anti-B12 antibody concentration, the solution assay was inhibited only 22% and there was no decrease in color development with the membrane spot. A decrease in color development on the membrane was observed with the immune complexes formed with higher anti-B12 antibody concentrations, which correlated with the increase in inhibition of complementation (55 to 64% inhibition with 1:1000 to 1:100 anti-B12) in solution assay. To "open up" this assay, the immune complex (1:2000 anti-B12) was incubated with 5 to 100 nM B12 before assay and spotting. The complex was inhibited 44% without analyte dose and 34% with the highest B12 concentration, indicating that the ratio of ED-B12 and anti-B12 needed optimization. However, the area of color development was affected only slightly by the presence of an analyte dose. The color density out to the solvent front was identical with the no analyte sample, while there was a slight increase in density in the very center. From this data, it is evident that a sensitive assay could be developed for B12 once the concentrations of the various components have been optimized.

As demonstrated by the above examples and description, the subject invention provides for a convenient, accurate and rapid method for determining a wide variety of ligands. The protocols are simple and do not require technical competence to perform the various steps. In addition, formats are provided which allow for visual determination of the result, without requiring expensive equipment or the need to use equipment to obtain the result.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of a ligand or receptor analyte in a sample employing (1) complementary fragments of beta-galactosidase, which fragments are defined as enzyme acceptor (EA) and enzyme donor (ED) and form a complex of active enzyme when bound to each other, (2) a bibulous support to which a first one of said fragments is substantially uniformly bound in a detection region, and (3) a conjugate comprising the second one of said fragments jointed to a moiety cross-reactive with a ligand analyte or complementary to a receptor analyte, said method comprising:

combining in an assay medium (1) said sample, (2) said conjugate, and, when said analyte is a ligand, (3) a receptor reagent capable of binding said ligand, and incubating said assay medium for a sufficient time for ligand to bind to receptor reagent or receptor analyte present in said assay medium, wherein said conjugate is hydrophilic and complexes of said conjugate with said receptor reagent or said receptor analyte are prevented form binding to said first one of said fragments in said detection region (1) by separating complexed enzyme fragment conjugate from uncomplexed enzyme conjugate prior to contacting said bibulous support by using a receptor bound to another support or (2)

by locating an anti-receptor on the bibulous support so that complexed enzyme fragment conjugate binds to said anti-receptor to form a high molecular weight aggregate which cannot migrate to said detection region and therefore cannot form active enzyme;

adding said assay medium to a receiving site of said bibulous support whereby said assay medium wicks away from said receiving site into said detection region;

contacting said detection region wit a substrate for beta-galactosidase to produce a product which provides a change in a detectable signal; and relating said change to the presence of analyte in said sample.

2. A method according to claim 1, wherein said EA is bound to said bibulous support.

3. A method according to claim 1, wherein said bibulous support is elongated, said receiving site is proximal to one end of said bibulous support, and said relating comprises determining the distance from the receiving site at which a change in said detectable signal is observed.

4. A method according to claim 1, wherein said bibulous support is of a relatively symmetrical two-dimensional shape, said receiving site is relatively centrally located on said bibulous support, and the relating comprises determining the distance from the receiving site at which a change in said detectable signal is observed.

5. A method according to claim 1, wherein said bibulous support is a nylon membrane.

6. A method according to claim 1, wherein said bibulous support is allowed to substantially dry after contacting.

7. A method for detecting the presence of a ligand or receptor analyte in a sample employing (1) complementary fragments of beta-galactosidase, which fragments are defined as enzyme acceptor (EA) and enzyme donor (ED) and form a complex of active enzyme, when bound to each other, (2) an elongated bibulous support to which EA is substantially uniformly bound in a detection region, and (3) a conjugate comprising ED joined to a moiety cross-reactive with a ligand analyte or complementary to a receptor analyte, said method comprising:

combining in an assay medium, said sample, (2) said conjugate, and, when said analyte is a ligand, (3) a receptor reagent capable of binding said ligand, and incubating said assay medium for a sufficient time for ligand to bind to receptor reagent or receptor analyte present in said assay medium, wherein said conjugate is hydrophilic and complexes of said conjugate with said receptor reagent or said receptor analyte are prevented form binding to said EA in said detection region (1) by separating complexed enzyme fragment conjugate form uncomplexed enzyme conjugate prior to contacting said bibulous support by using a receptor bound to another support or (2) by locating an anti-receptor on the bibulous support so that complexed enzyme fragment conjugate binds to said antireceptor to form a high molecular weight aggregate which cannot migrate to said detection region and therefore cannot form active enzyme;

adding said assay medium to a receiving site of said bibulous support whereby said assay medium wicks away from said receiving site into said detection region;

contacting said detection region with a substrate for beta-galactosidase to produce a product which provides a change in a detectable signal; and determining the distance or color intensity form said receiving site at which a change in said detectable signal is observed.

8. A method according to claim 7, wherein said bibulous support is a nylon membrane.

9. A method according to claim 7, wherein said complexes of said receptor reagent or receptor are prevented from binding to EA in said detection region by binding said receptor reagent or receptor to a support.

10. A method according to claim 7, wherein said complexes of said receptor reagent or receptor are prevented from binding to EA in said detection region by binding said receptor reagent or receptor to a second antibody specific for said receptor reagent or said receptor.

* * * * *